(12) United States Patent
Aulwurm et al.

(10) Patent No.: US 8,776,624 B2
(45) Date of Patent: Jul. 15, 2014

(54) SAMPLE PREPARATION SYSTEM AND A METHOD FOR PROCESSING A SAMPLE

(76) Inventors: Uwe Aulwurm, Velden/Vils (DE); Michael Baumann, Dorfen (DE)

( * ) Notice: Subject to any disclaimer, the term of this patent is extended or adjusted under 35 U.S.C. 154(b) by 375 days.

(21) Appl. No.: 13/108,304

(22) Filed: May 16, 2011

(65) Prior Publication Data

US 2012/0042736 A1 Feb. 23, 2012

(30) Foreign Application Priority Data

Aug. 20, 2010 (DE) .......................... 10 2010 037 084

(51) Int. Cl.
*G01N 35/10* (2006.01)
*G01N 1/34* (2006.01)

(52) U.S. Cl.
CPC ...... *G01N 35/109* (2013.01); *G01N 2035/1053* (2013.01); *G01N 1/34* (2013.01)
USPC ..................................................... 73/864.25

(58) Field of Classification Search
CPC .............................................. B01J 2219/00585
USPC ............... 73/864.21, 864.22, 864.23, 864.24, 73/864.25
See application file for complete search history.

(56) References Cited

U.S. PATENT DOCUMENTS

| | | | | |
|---|---|---|---|---|
| 3,666,420 A | * | 5/1972 | Paatzsch | 422/81 |
| 4,523,484 A | * | 6/1985 | Kadota et al. | 73/864.12 |
| 4,830,832 A | * | 5/1989 | Arpagaus et al. | 422/65 |
| 5,055,263 A | * | 10/1991 | Meltzer | 422/65 |
| 5,216,926 A | | 6/1993 | Lipscomb | |
| 5,301,261 A | | 4/1994 | Poole et al. | |
| 5,443,792 A | | 8/1995 | Buhler | |
| 5,471,873 A | * | 12/1995 | Nyce et al. | 73/453 |
| 5,474,744 A | * | 12/1995 | Lerch | 422/510 |
| 5,529,754 A | | 6/1996 | Bonacina et al. | |
| 5,783,450 A | | 7/1998 | Yoshida et al. | |
| 6,143,252 A | * | 11/2000 | Haxo et al. | 506/40 |
| 6,228,659 B1 | * | 5/2001 | Kowallis et al. | 436/180 |
| 6,387,330 B1 | * | 5/2002 | Bova et al. | 422/509 |
| 6,599,479 B1 | * | 7/2003 | Kietzmann et al. | 422/502 |
| 6,913,934 B2 | * | 7/2005 | Dales et al. | 436/180 |
| 7,270,788 B2 | * | 9/2007 | Meyer et al. | 422/510 |
| 7,469,606 B1 | * | 12/2008 | Wiederin | 73/864.24 |
| 7,470,402 B2 | * | 12/2008 | Abou Saleh et al. | 422/606 |
| 7,529,598 B2 | * | 5/2009 | Ingenhoven et al. | 700/245 |
| 8,197,754 B2 | * | 6/2012 | Yanami et al. | 422/64 |
| 2003/0039589 A1 | * | 2/2003 | Smith | 422/100 |
| 2003/0188588 A1 | * | 10/2003 | Jaeger | 73/863.84 |
| 2004/0027656 A1 | * | 2/2004 | Ue | 359/392 |

(Continued)

FOREIGN PATENT DOCUMENTS

| | | |
|---|---|---|
| DE | 224682 | 7/1985 |
| DE | 4210963 A1 | 10/1993 |
| DE | 10321753 A1 | 12/2004 |
| EP | 0601213 A1 | 6/1994 |

*Primary Examiner* — John Fitzgerald
(74) *Attorney, Agent, or Firm* — Renner Kenner Greive Bobak Taylor & Weber

(57) ABSTRACT

The sample preparation system according to the invention comprises substantially a transport mechanism movable in the x, y and z directions, which at a first retaining fixture has a sampler for taking up samples that is movable in the z direction and at a second retaining fixture supports a processing apparatus for processing samples that is movable in the z direction, wherein the sampler is connected via at least one connecting line to the processing apparatus for fluid exchange.

10 Claims, 1 Drawing Sheet

(56) References Cited

U.S. PATENT DOCUMENTS

| | | |
|---|---|---|
| 2005/0079073 A1* | 4/2005 | Abou-Saleh et al. ......... 417/415 |
| 2006/0012773 A1 | 1/2006 | Schutze et al. |
| 2007/0186648 A1* | 8/2007 | Harmon et al. ................. 73/319 |
| 2009/0227006 A1* | 9/2009 | Kopp et al. ................. 435/287.2 |
| 2011/0090088 A1* | 4/2011 | Kenney et al. ................ 340/623 |

* cited by examiner

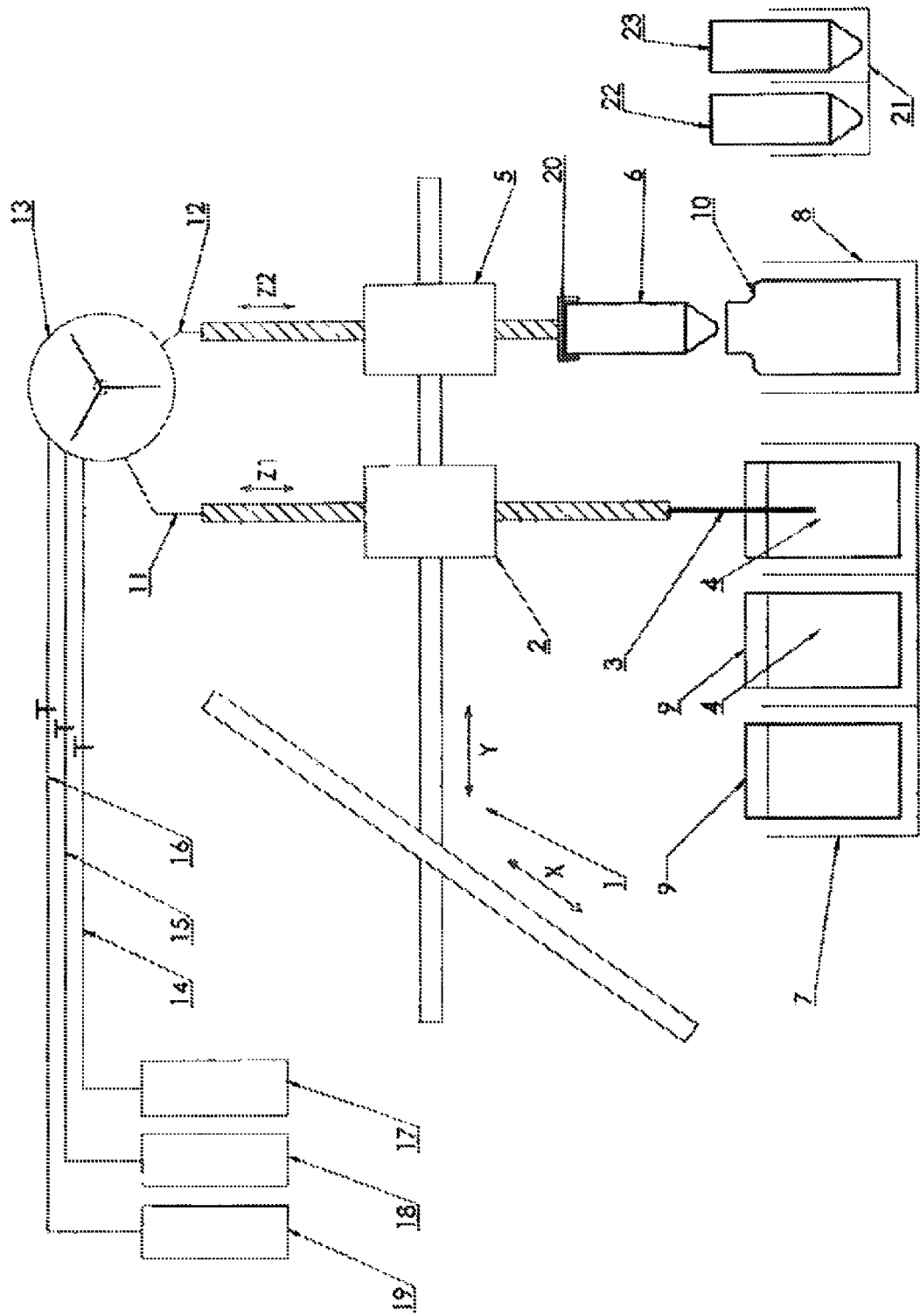

SAMPLE PREPARATION SYSTEM AND A METHOD FOR PROCESSING A SAMPLE

FIELD OF THE INVENTION

The invention relates to a sample preparation system and to a method for processing a sample using such a sample preparation system.

BACKGROUND OF THE INVENTION

A wide variety of systems for preparing samples are known from practical fields of operation. They comprise a transport mechanism movable in the x, y and z directions, which at first retaining fixture holds a sampler for taking up samples that is movable in the z direction and at a second retaining fixture holds a processing apparatus for processing samples that is movable in the z direction.

The sampler is formed, for example, by a needle, and enables a sample to be taken from a sample vessel, and then to be moved to a processing apparatus and transferred thereto. The processing apparatus can be gripped by means of the second retaining fixture and transferred by means of the transport mechanism to a desired location. Normally, supports hold a large number of sample vessels ready, which have to be approached and processed in the above described manner in succession.

The invention addresses the problem of specifying a sample preparation system as well as a method for processing samples, which is distinguished in that handling is more flexible and faster.

SUMMARY OF THE INVENTION

According to the invention this problem is solved by the features of claim 1.

The sample preparation system according to the invention essentially comprises a transport mechanism movable in the x, y and z directions, which at a first retaining fixture has a sampler movable in the z direction for taking up samples and at a second retaining fixture has a processing apparatus movable in the z direction for processing samples, the sampler being connected via at least one connecting line to the processing apparatus for fluid exchange.

The term "fluid exchange" means any exchange of gaseous or liquid samples. Owing to the connecting line between sampler and processing apparatus, no movement of the transport mechanism is needed for transfer of the sample from the sampler to the processing apparatus. In this way, the sample enters the processing apparatus very easily and quickly. Furthermore, the transport mechanism is protected. Moreover, in this way the sample to be transferred can be prevented from being accidentally spilt over the working plane of the transport mechanism and thereby contaminating the system and other samples.

In the method according to the invention for processing a sample, the above described sample preparation system is used as follows:

the sampler is positioned in the z direction above a sample vessel, the sampler removes a sample from the sample vessel, and the removed sample is supplied directly via the connecting line to the processing apparatus for processing the sample.

The sample preparation system can be used, for example, for preparing samples for analysis of foods and animal feedstuffs, environmental and pharmaceutical samples and the like.

Further embodiments of the invention form the subject matter of the subsidiary claims.

The sampler may be, for example, a needle or a different instrument with which the sample can be taken. A filter, a column, or a cartridge are suitable as the processing apparatus. According to a further embodiment of the invention, the processing apparatus is connected via connecting lines to a plurality of fluid containers, which contain, for example, organic solvents (such as e.g. petroleum ether, n-hexane) or other gaseous or liquid fluids that are required for preparing the processing apparatus or for preparing the sample. The fluid containers as well as the sampler are expediently connected via a pump mechanism to the processing apparatus attached to the second retaining fixture.

According to a further embodiment of the invention, at least one sample vessel and at least one sample-receiving container are arranged spatially adjacent in such a way that the sampler is arranged in the z direction above the sample vessel and the processing apparatus is arranged simultaneously above the sample-receiving container. In this way, it is possible to remove a sample from the sample vessel, to convey it directly to the processing apparatus via the connecting line, to process the sample in the processing apparatus and then deliver it to the sample-receiving container, without the sampler or the processing apparatus having to be moved.

Further advantages and constructions of the invention are explained in detail hereafter by means of the description and the drawing.

BRIEF DESCRIPTION OF THE DRAWINGS

FIG. 1 is a schematic representation of the sample preparation system in accordance with this invention.

DETAILED DESCRIPTION OF THE ILLUSTRATIVE EMBODIMENTS

It comprises substantially a transport mechanism 1 movable in the x, y and z directions, which comprises at a first retaining fixture 2 a sampler 3 for receiving samples that is movable in the z direction $z_1$ and at a second retaining fixture 5 comprises a processing apparatus 6 for processing samples that is movable in the z direction $z_2$. The second retaining fixture 5 can also be mounted on a second y-arm of the transport mechanism.

The sampler 3 is formed, for example, by a needle or a different element for taking up a sample. The processing apparatus 6 is, for example, a filter, a column or a cartridge, which is suitable for processing samples. The sample preparation system additionally comprises one or more supports 7, 8, which hold one or more objects, such as sample vessels 9 and sample-receiving containers 10. The supports are, for example, fastened side by side on a rail or positioned at predetermined positions on a platform. The objects arranged in the supports 7, 8 can be approached by the sample-taker and the processing apparatus 6, to enable a sample 4 to be removed and delivered respectively. The samples are, for example, liquid or solid substances.

The sampler 3 is connected via connecting lines 11, 12 to the processing apparatus 6 such that a sample 4 taken up by the sampler 3 can be transferred via the connecting lines 11, 12 to the processing apparatus, wherein a pump mechanism 13 can be inserted between the lines 11 and 12. The processing apparatus 6 and the sampler 3 is furthermore connected via connecting lines 14, 15 and 16 to a plurality of fluid containers 17, 18 and 19, the connecting lines 14, 15 and 16 and the connecting line 11 being coupled to corresponding connections of the pump mechanism 13 and the connecting line 12 directly connected to the processing apparatus 6 being coupled to a further connection of the pump mechanism 13.

Fluids that are needed for preparing the processing apparatus 6 and/or for processing the sample are held in the fluid containers 17 to 19. They may be, for example, organic solvents, such as, for example, petroleum ether, n-hexane, or other liquid or gaseous fluids.

The second retaining fixture 5 has a suitable gripper 20, which can be used to take hold of the required processing apparatus 6, 22, or 23 from a support 21. A sealing mechanism, not shown more specifically, that is also provided ensures a gas-tight and/or liquid-tight joint between processing apparatus and connecting line 12.

Processing of a sample is explained in the following using the example of the method for determining the hydrocarbon index in water:

For the purposes of the processing, it is assumed that the sample vessel 9 contains 50 ml of organic solvent (such as, for example, petroleum ether, n-hexane), in which an extracted sample is dissolved. A sample-receiving container 10 is located in the immediate vicinity. Using the transport mechanism, first of all the support 21 is approached and the processing apparatus 6 is removed by the gripper 20, the processing apparatus 6 being sealed in a gas-tight and/or liquid-tight manner by means of the sealing mechanism, not shown more specifically. The transport mechanism 1 now moves to the desired processing position, in which the sampler is located in the z-direction above the sample vessel 9 holding the sample 4 to be analysed. At the same time, the processing apparatus 6 is positioned in the z-direction above the sample-receiving container 10. The processing apparatus 6 is in this case a cartridge containing Florisil/sodium sulphate as filling material.

The transport mechanism 1 then moves the sampler 3 into the sample vessel 9 in order to aspirate the sample 4. The sample 4 taken up by the sampler 3 is now conveyed by means of the pump mechanism 13 via the connecting lines 11 and 12 into the processing apparatus 6, where impurities are separated from the sample. The sample thus purified is delivered by the processing apparatus 6 into the sample-receiving container 10. Then, via the pump mechanism, 5 to 10 ml of clean solvent is transferred for rinsing purposes from one of the liquid containers 17 to 19 into the sample vessel 9, and is then aspirated via the sampler 3 by means of the pump mechanism 13 and introduced directly via the processing apparatus 6 into the sample-receiving container 10. This process is repeated once again. The processing apparatus 6 can then by dried with nitrogen. The sample is now completely clean and a volume of 60 to 70 ml thereof is present in the sample-receiving container 10 for further processing.

The used processing apparatus is returned to the support 21. Using a special rinsing device, the sample preparation system now rinses the sampler 3, and also the second retaining fixture 5 with the gripper 20, by means of clean solvent, which is supplied via the pump mechanism 13. For that purpose the sampler and the second retaining fixture 5 are moved above a suitable collecting vessel, which collects the rinsing liquid. The sampling system is then ready for processing the next sample according to the same or a different procedure.

Because the sampler 3 and the processing apparatus 6 are in direct fluid exchange with one another via the line 11, the pump mechanism 13 and the line 12, a sample 4 can be taken up from a sample vessel 9, transferred to the processing apparatus 6 and from there delivered into a sample-receiving container 10, without the sampler 3 or the processing apparatus 6 having to be moved by the transport mechanism 1. The time that the transport mechanism would otherwise need for the movement is consequently saved. In addition, the medium to be transported is prevented from being accidentally spilt over the processing plane of the transport mechanism, thereby contaminating the system and other samples. In addition, the close proximity of sample vessel 9 and sample-receiving container 10 allows a direct correlation between starting and final samples.

Independently thereof, the sample-preparation system can also be used in the "classic" manner, i.e. a sample is removed from a sample vessel by means of the sampler 3 at location X and transferred to location Y and there processed by means of a processing apparatus.

A further example of the above-described sample-preparation system is that any number of liquids or gases can flow from "upstream" via the connecting lines 14, 15 and 16 through the processing apparatus 6. This means that these liquids need not be held ready in the working range of the transport mechanism, so that there is more space available there for processing apparatuses and sample vessels and sample-receiving containers.

The sampler 3 and the processing apparatus 6 can be moved using the transport mechanism into any position where admissions to the processing apparatus 6 can be charged either from downstream or from upstream via the connecting lines 14, 15 or 16.

The processing apparatus 6 can also be designed so that not only can it deliver a sample but can also take up a sample, in that the processing apparatus 6 is moved into a sample vessel 9 and aspirates the sample 4 from downstream and then delivers it again downstream at a different location. In this way the sample 4 is conducted twice through the processing apparatus 6, which is, for example, a cartridge.

The invention claimed is:

1. A sample preparation system having a transport mechanism movable in the x, y and z directions, which at a first retaining fixture has a sampler for taking up samples that is movable in the z direction and at a second retaining fixture has a processing apparatus for processing samples that is movable in the z direction, characterised in that the sampler is connected to the processing apparatus by at least on connecting line for fluid exchange.

2. A sample preparation system according to claim 1, characterised in that the sampler is a needle.

3. A sample preparation system according to claim 1, characterised in that the sampler is connected to the processing apparatus via a pump mechanism.

4. A sample preparation system according to claim 1, characterised in that the processing apparatus is a filter, a column or a cartridge.

5. A sample preparation system according to claim 1, characterised in that at least one sample vessel and at least one sample-receiving container are arranged spatially adjacent in such a way that the sampler is arranged in the z direction above the sample vessel and the processing apparatus is arranged simultaneously above the sample-receiving container.

6. A sample preparation system according to claim 1, characterised in that the second retaining fixture has a gripper for gripping the processing apparatus.

7. A sample preparation system according to claim 1, characterised in that at least one support is provided, in which one or more sample vessels and/or sample-receiving containers are mounted.

8. A sample preparation system according to claim 1, characterised in that the processing apparatus is connected to a plurality of fluid containers via connecting lines.

9. A sample preparation system according to claim 8, characterised in that the fluid containers are connected to the processing apparatus via a pump mechanism.

10. A method for processing a sample comprising the steps of:
- providing a sample preparation system having a transport mechanism movable in the x, y and z directions, which at a first retaining fixture has a sampler for taking up samples that is movable in the z direction and at a second retaining fixture has a processing apparatus for processing samples that is movable in the z direction, characterised in that the sampler is connected to the processing apparatus by at least on connecting line for fluid exchange, and further characterised in that at least one sample vessel and at least one sample-receiving container are arranged spatially adjacent in such a way that the sampler is arranged in the z direction above the sample vessel and the processing apparatus is arranged simultaneously above the sample-receiving container;
- positioning the sampler in the z direction above the sample vessel;
- removing a sample from the sample vessel with said sampler; and
- supplying the removed sample directly to the processing apparatus via the connecting line.

* * * * *